(12) United States Patent
Woo et al.

(10) Patent No.: US 9,671,352 B2
(45) Date of Patent: Jun. 6, 2017

(54) REEL-TO-REEL INSPECTION APPARATUS AND INSPECTION METHOD USING THE SAME

(71) Applicant: HAESUNG DS CO., LTD., Changwon-Si (KR)

(72) Inventors: Suck-Ha Woo, Changwon (KR); Je-Youn Jee, Changwon (JP); Ki-Sang Moon, Changwon (JP)

(73) Assignee: HAESUNG DS CO., LTD, Changwon-si (KR)

( * ) Notice: Subject to any disclaimer, the term of this patent is extended or adjusted under 35 U.S.C. 154(b) by 907 days.

(21) Appl. No.: 13/937,345

(22) Filed: Jul. 9, 2013

(65) Prior Publication Data
US 2014/0146163 A1   May 29, 2014

(30) Foreign Application Priority Data

Nov. 23, 2012 (KR) .......................... 10-2012-0133936

(51) Int. Cl.
    G06K 9/00     (2006.01)
    G01N 21/89    (2006.01)
(52) U.S. Cl.
    CPC ............................... *G01N 21/8901* (2013.01)
(58) Field of Classification Search
    None
    See application file for complete search history.

(56) References Cited

U.S. PATENT DOCUMENTS

| | | | | |
|---|---|---|---|---|
| 5,732,529 A * | 3/1998 | Dey | .................. | B65H 23/0326 53/389.2 |
| 5,966,218 A * | 10/1999 | Bokelman | .............. | G01N 21/95 356/429 |
| 6,259,526 B1 * | 7/2001 | Pace | .................. | G01N 21/8983 356/238.1 |
| 6,576,390 B1 * | 6/2003 | Shimizu | ................. | G03B 17/26 396/518 |

(Continued)

FOREIGN PATENT DOCUMENTS

| | | |
|---|---|---|
| CN | 2747205 Y | 12/2005 |
| CN | 1808058 A | 7/2006 |

(Continued)

OTHER PUBLICATIONS

Communication dated Aug. 1, 2016, from the State Intellectual Property Office of People's Republic of China in counterpart Application No. 201310586920.1.

(Continued)

*Primary Examiner* — Soo Park
(74) *Attorney, Agent, or Firm* — Sughrue Mion, PLLC

(57) ABSTRACT

Provided are a reel-to-reel inspection apparatus and method. The reel-to-reel inspection apparatus includes: an unwinding unit configured to unwind a roll-shaped object; a first inspection unit configured to photograph a surface of the object discharged from the unwinding unit; a second inspection unit configured to photograph another surface of the object which has passed through the first inspection unit; a marking unit configured to indicate a mark on the object which has passed through the second inspection unit; and a winding unit configured to wind in a roll shape the object which has passed through the marking unit.

16 Claims, 10 Drawing Sheets

(56) References Cited

U.S. PATENT DOCUMENTS

| | | | | |
|---|---|---|---|---|
| 6,919,965 | B2* | 7/2005 | Koele | A61F 13/15756 |
| | | | | 156/351 |
| 7,123,765 | B2* | 10/2006 | Carbone, II | G06T 7/0004 |
| | | | | 382/141 |
| 7,590,279 | B2 | 9/2009 | Akiyama | |
| 7,695,592 | B2* | 4/2010 | Shakespeare | G01N 21/8806 |
| | | | | 162/198 |
| 8,000,501 | B2* | 8/2011 | Huotilainen | G01N 21/8983 |
| | | | | 382/108 |
| 9,073,304 | B2* | 7/2015 | Headley | B41F 33/0036 |
| 9,216,861 | B2* | 12/2015 | Adachi | H01M 10/0409 |
| 9,235,884 | B2* | 1/2016 | Ogasawara | A61F 13/15658 |
| 2001/0038709 | A1* | 11/2001 | Bett | G06T 7/0004 |
| | | | | 382/141 |
| 2003/0024301 | A1* | 2/2003 | Graeffe | G01B 11/0691 |
| | | | | 73/37.6 |
| 2004/0178296 | A1 | 9/2004 | Wild et al. | |
| 2006/0237156 | A1* | 10/2006 | Shakespeare | G01N 21/8806 |
| | | | | 162/198 |
| 2010/0162865 | A1* | 7/2010 | Innocenzo | B65H 18/28 |
| | | | | 83/73 |
| 2011/0050879 | A1* | 3/2011 | Shyy | G01N 21/8806 |
| | | | | 348/88 |
| 2011/0083791 | A1* | 4/2011 | Nakazono | G01N 21/8914 |
| | | | | 156/64 |
| 2014/0190362 | A1* | 7/2014 | Weidmann | B41F 33/0036 |
| | | | | 101/407.1 |

FOREIGN PATENT DOCUMENTS

| | | |
|---|---|---|
| CN | 1828217 A | 9/2006 |
| CN | 201046873 Y | 4/2008 |
| CN | 201177605 Y | 1/2009 |
| CN | 101609054 A | 12/2009 |
| CN | 201434848 Y | 3/2010 |
| CN | 201834608 U | 5/2011 |
| CN | 202138890 U | 2/2012 |
| CN | 202533374 U | 11/2012 |
| JP | 2007205828 A | 8/2007 |
| KR | 10-2007-0069550 A | 7/2007 |
| KR | 1020070119868 A | 12/2007 |
| KR | 10-2008-0009628 A | 1/2008 |
| KR | 1020100046601 A | 5/2010 |
| KR | 1020110026920 A | 3/2011 |
| WO | 2008/004256 A1 | 1/2008 |

OTHER PUBLICATIONS

Communication dated Mar. 8, 2017, from the State Intellecutual Property Office of People's Republic of China in counterpart Application No. 201310586920.1.

* cited by examiner

REEL-TO-REEL INSPECTION APPARATUS AND INSPECTION METHOD USING THE SAME

CROSS-REFERENCE TO RELATED PATENT APPLICATION

This application claims priority from Korean Patent Application No. 10-2012-0133936, filed on Nov. 23, 2012, in the Korean Intellectual Property Office, the disclosure of which is incorporated herein in its entirety by reference.

BACKGROUND

1. Field

Apparatuses and methods consistent with exemplary embodiments relate to reel-to-reel inspection of roll-shaped products.

2. Description of the Related Art

Inspection apparatuses for visually inspecting planar products such as printed circuit boards (PCBs) or flexible PCBs have been widely used in many industrial fields. These inspection apparatuses are classified into panel type inspection apparatuses for inspecting sheet-shaped objects which are discontinuously fed to the inspecting apparatuses, and reel-to-reel type inspection apparatuses for inspecting roll-shaped objects which are also continuously fed to the inspecting apparatuses.

Since reel-to-reel type inspection apparatuses are used to inspect objects while continuously feeding the objects, an inspection speed is fast. Also, when the inspection is completed, the objects may be wound again in a roll shape to improve distribution and handling efficiencies. Also, as the demand for flexible roll-shaped electronic components such as PCBs has increased in recent years, the need for reel-to-reel type inspection apparatuses has also increased.

Such a reel-to-reel inspection apparatus may be used to inspect one surface or both surfaces of an object. In the case where both surfaces of an object are inspected, the surfaces are inspected sequentially. That is, after the inspection on one surface of the object is completed, the inspection on the other surface of the object is performed. Therefore, the inspection processes may be separately performed, and in some cases, a process for turning over the object may be required.

SUMMARY

One or more exemplary embodiments provide a reel-to-reel inspection apparatus for inspecting both surfaces of a roll-shaped target object at the same time in order to simply and quickly perform an inspection process, and a reel-to-reel inspection method.

According to an aspect of an exemplary embodiment, there is provided a reel-to-reel inspection apparatus including: an unwinding unit configured to unwind a roll-shaped object; a first inspection unit configured to photograph a surface of the object discharged from the unwinding unit; a second inspection unit configured to photograph another surface of the object which has passed through the first inspection unit; a marking unit configured to indicate a mark on the object which has passed through the second inspection unit; and a winding unit configured to wind in a roll shape the object which has passed through the marking unit.

The unwinding unit may include: a roll mount part configured to mount the object and move in a width direction of the object; an alignment inspection part configured to detect a movement of the object in a direction crossing the unwound direction the object; and a control part configured to move the roll mount part in response to the movement of the object detected by the alignment inspection part.

The roll mount part of the unwinding unit may vacuum-absorb the object.

A buffer dancer roller pressing the object may be disposed at at least one portion between the unwinding unit, the first inspection unit, the second inspection unit, and the winding unit to apply a tensile force to the object.

The buffer dancer roller may press the object via its weight, and a weight balancing part applying a force to the buffer dancer roller in a direction opposite to the gravity may be provided to offset a portion of the weight of the buffer dancer roller.

The weight balancing part may include: a belt connected to a side of the buffer dancer roller; a pulley driving the belt to move the buffer dancer roller connected to the side of the belt; and a weight connected to other side of the belt to apply a force to the buffer dancer roller in a direction opposite to gravity.

The buffer dancer roller may be disposed to be movable in a direction crossing a transfer direction of the object, and the reel-to-reel inspection apparatus may further include a detection part detecting a position of the buffer dancer roller.

The reel-to-reel inspection apparatus may further include: a belt having a side connected to the buffer dancer roller; and a pulley driving the belt to move the buffer dancer roller connected to the side of the belt, wherein the detection part may include a rotary encoder disposed on the pulley.

The reel-to-reel inspection apparatus may further include a weight connected to other side of the belt to offset the weight of the buffer dancer roller.

The first inspection unit may include: a first camera photographing the surface of the object; and a first vacuum plate absorbing the other surface of the object, wherein the second inspection unit may include: a second camera photographing the other surface of the object; and a second vacuum plate absorbing the surface of the object.

The second vacuum plate of the second inspection unit may be disposed above the object, and the second camera of the second inspection unit may be disposed under the object, wherein the reel-to-reel inspection apparatus may further include an auxiliary press roller upwardly pushing at least one side of the object corresponding to at least one side of the second vacuum plate so that the at least one side of the object is disposed at a position higher than that of a surface of the second vacuum plate.

The first inspection unit may include a first reciprocating roller disposed on at least one side of front and rear sides of the first vacuum plate to be movable between a first position at which the object contacts the first vacuum plate and a second position at which the object is spaced from the first vacuum plate, and the second inspection unit may include a second reciprocating roller disposed on at least one side of front and rear sides of the second vacuum plate to be movable between a first position at which the object contacts the second vacuum plate and a second position at which the object is spaced from the second vacuum plate.

At least one of the first and second cameras may be disposed movable in at least one direction of a length direction of the object and a width direction of the object, wherein the reel-to-reel inspection apparatus may further include a lighting part coupled to at least one of the first and second cameras and integrally moving with the at least one camera to emit light onto the object.

The lighting part may include: a translucent mirror disposed between at least one of the first and second cameras and the object; and a side lighting unit emitting light onto the translucent mirror, wherein the light emitted from the side lighting unit may be reflected by the translucent mirror onto the object, and the light reflected by the object may pass through the translucent mirror and become incident onto at least one of the first and second cameras.

According to another aspect of the present invention, there is provided a reel-to-reel inspection method including: unwinding a roll-shaped object; photographing a surface of the unwound object to inspect the surface; photographing another surface of the object; determining whether a defect exists on the object according to inspection results of the surface inspection process and the other surface inspection process; marking existence or nonexistence of the defect on the object after the determining; and winding the object, on which the existence or nonexistence of the defect is marked, in a roll shape.

The surface inspection process may further include absorbing the object onto a first vacuum plate to inspect the surface, and the other surface inspection process may further include absorbing the object onto a second vacuum plate to inspect the other surface.

The reel-to-reel inspection method may further include increasing or decreasing the length of the moving path of the object disposed on at least one portion between an unwinding unit, a first inspection unit, a second inspection unit, a marking unit, and a winding unit.

A buffer dancer roller may be movably disposed in a direction crossing a moving path of the object to increase or decrease a length of the moving path of the object.

The reel-to-reel inspection method may further include: detecting a position of the buffer dancer roller in the direction crossing the moving path of the object; and synchronizing at least two operations of the unwinding the roll-shaped object, the photographing the surface of the object, the photographing the other surface of the object, the determining whether the defect exists, the marking the existence or nonexistence, and winding the object, based on information about the detected position of the buffer dancer roller.

At least one of the inspecting the surface and the inspecting the other surface may include scanning the object while an inspection apparatus for the inspecting is moving in length and width directions of the object, and wherein the scanning the object may include removing foreign matters from at least one of the surface and the other surface of the object by using a blower coupled to the inspection apparatus and integrally moving with the camera.

BRIEF DESCRIPTION OF THE DRAWINGS

The above and other features will become more apparent by describing in detail exemplary embodiments with reference to the attached drawings, in which.

DETAILED DESCRIPTION OF THE EXEMPLARY EMBODIMENTS

Hereinafter, a reel-to-reel inspection apparatus according to exemplary embodiments will be described with reference to the accompanying drawings.

Figure 1:
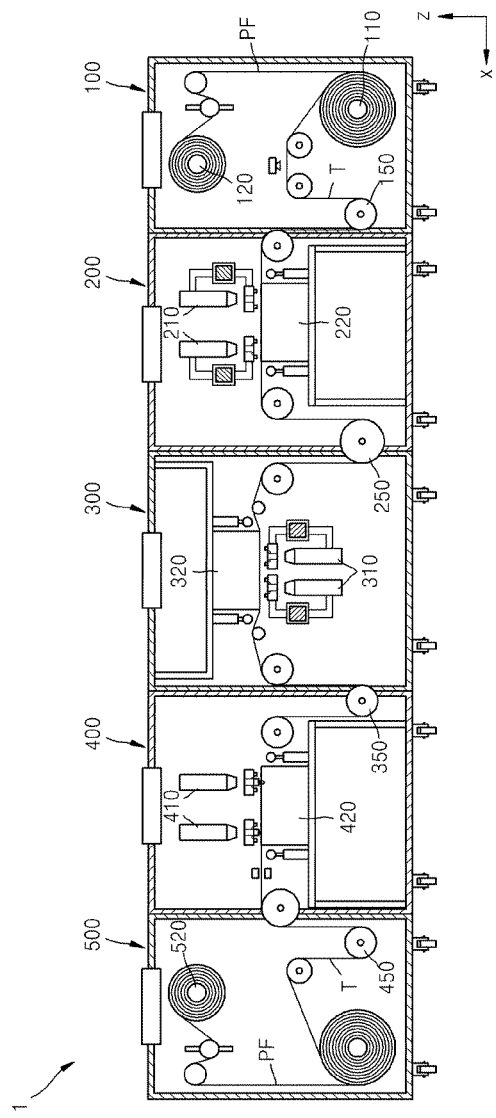
FIG. 1 is a schematic view of a reel-to-reel inspection apparatus according to an exemplary embodiment.

FIG. 1 is a schematic view of a reel-to-reel inspection apparatus 1 according to an exemplary embodiment. Referring to FIG. 1, the reel-to-reel inspection apparatus 1 includes an unwinding unit 100, a first inspection unit 200, a second inspection unit 300, a marking unit 400, and a winding unit 500. In the reel-to-reel inspection apparatus 1 according to the current embodiment, the unwinding unit 100, the first inspection unit 200, the second inspection unit 300, the marking unit 400, and the winding unit 500 may be integrally assembled in one or more units as necessary. Alternatively, the unwinding unit 100, the first inspection unit 200, the second inspection unit 300, the marking unit 400, and the winding unit 500 may be provided as units separated from each other as necessary.

When a roll-shaped object T is mounted on the unwinding unit 100, the unwinding unit 100 may release and unwind the object T. The object T according to the current embodiment may be any roll-shaped object. For example, the object T may be a flexible PCB or a flexible display. In the current embodiment, the object T may have a width of about 510 mm. Also, a feed speed of the object T may be set to be about 1.2 meters per minute.

Figure 2:
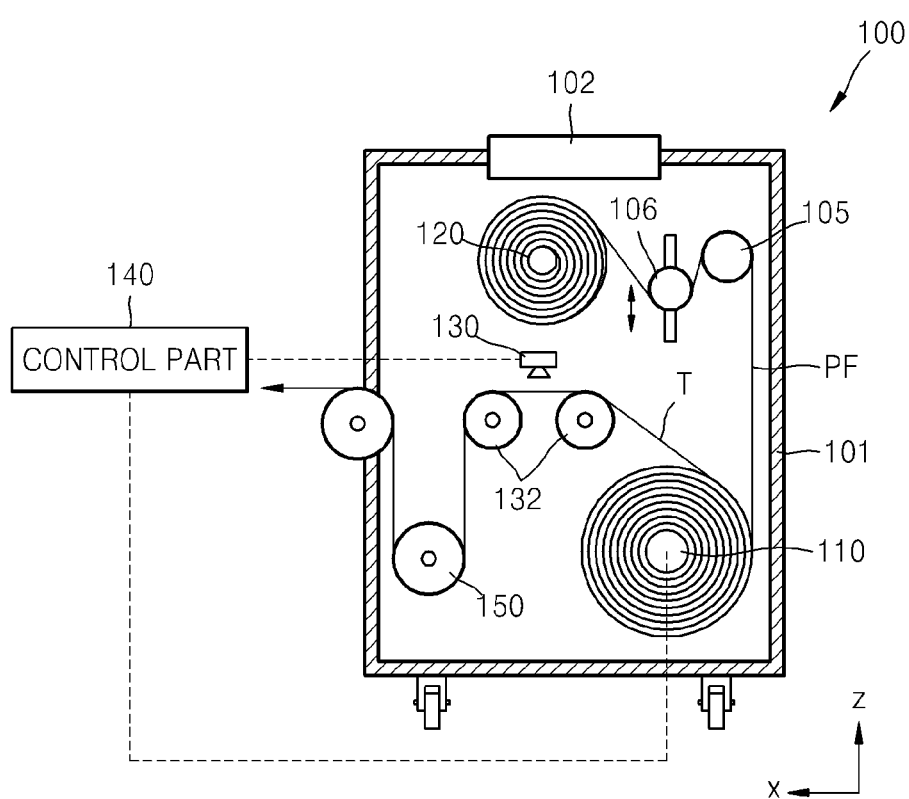
FIG. 2 is a schematic view illustrating an unwinding unit of the reel-to-reel inspection apparatus of FIG. 1, according to an exemplary embodiment.

FIG. 2 is a schematic view of the unwinding unit 100. Referring to FIG. 2, the unwinding unit 100 includes a housing 101, a roll mount part 110, a protection film roll mount part 120, an alignment inspection part 130, and a control part 140.

The housing 101 accommodates the roll mount part 110, the protection film roll mount part 120, and the alignment inspection part 130 therein. Also, a high efficiency particulate air (HEPA) filter 102 is disposed in an upper portion of the housing 101. The HEPA filter 102 sucks air at an upper side of the housing 101 and forcibly flows the air in the housing 101. Also, the HEPA filter 102 filters fine foreign matters contained in the air. Also, the HEPA filter 101 forcibly moves the air toward a lower side of the housing 101 to maintain a downstream flow of the air within the housing 101. When the downstream flow is generated within the housing 101 as described above, floating matters contained in the air within the housing 101 may sink to the bottom of the housing 101. Thus, the interior of the housing 101 may be maintained in a highly clean state. However, the HEPA filter may be disposed in a different part of the housing 101, and flows and filters air in different ways, according to another exemplary embodiment.

Figure 3:
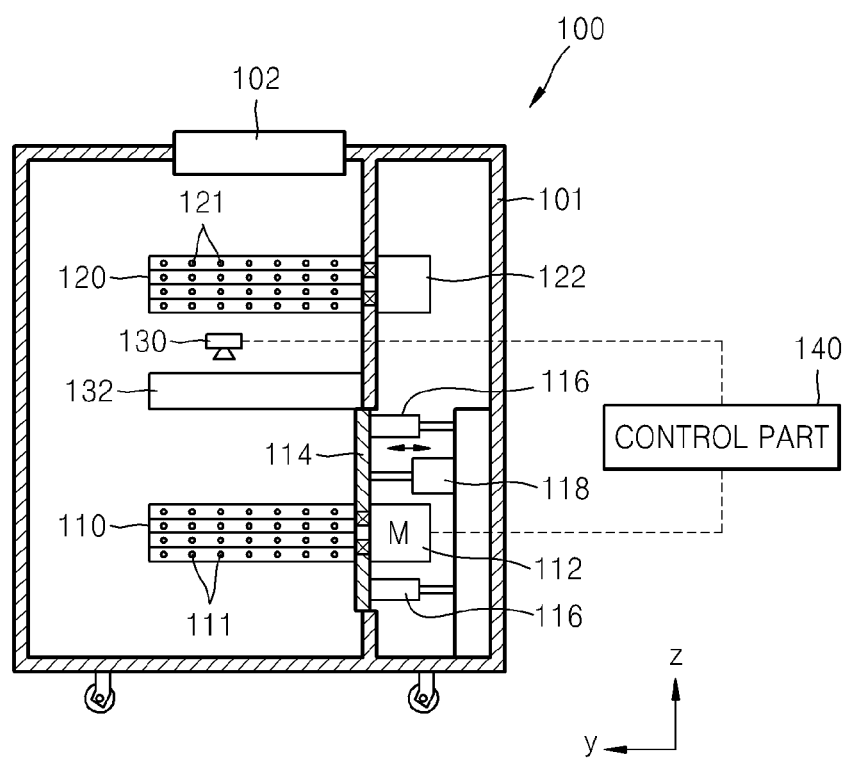
FIG. 3 is a schematic view illustrating the unwinding unit of the reel-to-reel inspection apparatus of FIG. 1 when viewed in the other direction, according to an exemplary embodiment.

The roll mount part 110 may be a part on which the object T having the roll shape is mounted. The roll mount part 110 rotatably supports the object T so that the object T is released while being rotated. FIG. 3 is a schematic view of the unwinding unit 100 of FIG. 2 when viewed in an unwinding direction (X direction) of the object T, assuming that the unwinding unit 100 does not include the buffer dancer roller 105 and 106 described below. Referring to FIG. 3, the roll mount part 110 has a plurality of absorption holes 111 in an outer surface thereof to prevent a roll of the object T from slipping. Thus, the roll mount part 110 may vacuum-absorb the roll of the object T. The rotation of the roll mount part 110 may be controlled by a motor 116.

The roll mount part 110 is coupled to the moving frame 114. The moving frame 114 may be moved forwardly or backwardly in a length direction of the roll mount part 110, i.e., in a width direction of the object T or the Y direction. The movement of the moving frame 114 may be guided in a straight line direction by a linear motion (LM) guide 116. Also, a movement amount of the moving frame 114 may be controlled by a linear actuator 118. Various linear driving devices such as a linear motor, a ball screw connected to a motor, an air piston, and the like may be used as the linear actuator 118. The linear actuator 118 is connected to the control part 140. Thus, an operation time and movement amount of the linear actuator 118 may be controlled by the control part 140. That is, the control part 140 may control the linear actuator 118 to control the position and movement of the roll mount part 110.

The protection film roll mount part 120 separates a protection film PF attached to one surface of the object T from the object T to wind the protection film PF. The protection film roll mount part 120 rotatably supports a roll of the protection film PF. Also, the protection film roll mount part 120 may have a plurality of absorption holes 121 to prevent the roll of the protection film PF from slipping from the protection film roll mount part 120 when the protection film roll mount part 120 is rotated. At least one buffer dancer roller 105 or 106 may be disposed on a moving path of the protection film PF between the roll mount part 110 and the protection film roll mount part 120 to adjust a tension of the protection film PF. The buffer dancer roller 105 or 106 may adequately press the protection film PF to apply a tensile force to the protection film PF. Also, the buffer dancer roller 106 may be moved to a position to adjust a length of the moving path of the protection film PF.

The alignment inspection part 130 detects variations in position and angle in a width direction of the object T unwound from the roll mount part 110. When a camera is used, the alignment inspection part 130 may visually detect the position of the object T. The alignment inspection part 130 transmits information with respect to the position of the object T to the control part 140. The control part 140 controls the movement of the roll mount part 110 so that the object T is moved within a predetermined range. For example, when the alignment inspection part 130 detects the object T biased in one direction, the control part 140 may move the roll mount part 110 in a direction opposite to the biased direction of the object T so that the object T returns to its original position. That is, the control part 140 may feedback-controls the roll mount part 110 by using the position of the object T detected by the alignment inspection part 130 to effectively prevent the object T from being biased from a reference position.

The control part 140 of the unwinding unit 100 may be provided separately from the unwinding unit 100 as shown in FIG. 3. Alternatively, the control part 140 may be integrated with a control unit 600 for an overall control of the reel-to-reel inspection apparatus 1 according to an exemplary embodiment.

The object T unwound from the roll mount part 110 is introduced into the first inspection unit 200 via a transfer roller 132 and a buffer dancer roller 150. The transfer roller 132 guides the movement of the object T and also allows a tensile force to act continuously on the object T. The buffer dancer roller 150 presses the moving object T so that a tensile force is applied to the object T. Also, the buffer dancer roller 150 is movably disposed in a direction crossing the movement direction of the object T to adjust a length of the moving path of the object T.

Figure 4:
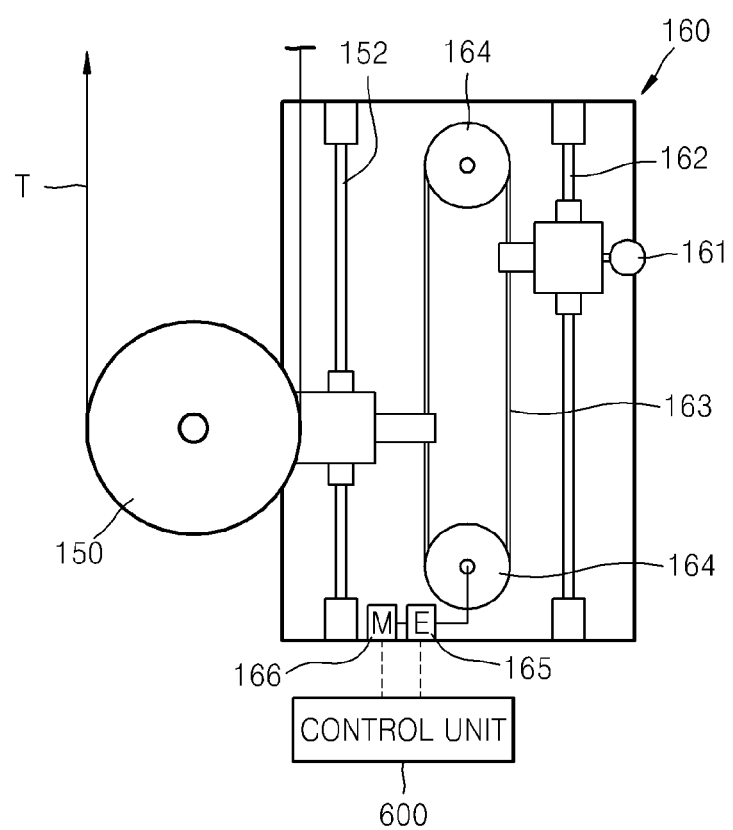
FIG. 4 is a schematic view illustrating a weight balancing part of the reel-to-reel inspection apparatus of FIG. 1, according to an exemplary embodiment.

FIG. 4 is a schematic view illustrating an example of the buffer dancer roller 150. Referring to FIG. 4, the buffer dancer roller 150 is connected to a weight balancing part 160 to apply a predetermined pressure into the object T. The weight balancing part 160 includes a first LM guide 152, a second LM guide 162, a pulley 164, a belt 163, a pulley driving motor 166, a buffer dancer roller position detection part, and a weight 161.

The first LM guide 152 guides movement of the buffer dancer roller 150 in a direction crossing the movement direction of the object T, e.g., in a vertical direction.

The second LM guide 162 guides movement of the weight 161 in a direction crossing the movement of the object T, e.g., in a vertical direction or the Z direction.

The pulley 164 and the belt 163 are disposed between the first LM guide 152 and the second LM guide 162. The buffer dancer roller 150 is coupled to a side of the belt 163, and the weight 161 is coupled to other side of the belt 163. Thus, when the pulley 164 is rotated, the belt 163 hung on the pulley 164 may be moved to move the buffer dancer roller 150 and the weight 161 which are coupled to the belt 163. Here, since the buffer dancer roller 150 and the weight 161 are disposed at sides opposite to each other with respect to the belt 163, the buffer dancer roller 150 and the weight 161 are moved in directions opposite to each other. For example, when the pulley 164 is rotated such that the buffer dancer roller 150 ascends, the weight 161 descends.

The buffer dancer roller 150 presses the object T by a self-weight thereof. If the buffer dancer roller 150 is too heavy, an excessive tension may be applied to the object T. In the case of the weight balancing part 160 according to the current embodiment, the weight 161 may be used to effectively adjust a pressure applied from the buffer dancer roller 150 to the object T because the weight 161 is connected to the buffer dancer roller 150 through the pulley 164 to pull the buffer dancer roller 150 in a direction opposite to a gravity direction. The weight 161 may be selected in consideration of a weight of the buffer dancer roller 150 and a tensile force to be applied to the object T.

The pulley driving motor 166 may drive the pulley 164 to change the position of the buffer dancer roller 150. The pulley driving motor 166 is back-drivable. The pulley driving motor 166 is connected to the control unit 600 to control the rotation of the pulley 164 according to a control signal of the control unit 600.

The buffer dancer roller position detection part detects the position of the buffer dancer roller 150 to transmit the detected position information to the control unit 600. In the current embodiment, the buffer dancer roller position detection part is embodied in a rotary encoder 165 connected to the pulley driving motor 166. The rotary encoder 165 detects a rotation amount of the pulley driving motor 166 to obtain position information of the buffer dancer roller 150 connected to the pulley 164. The information with respect to the rotation amount of the pulley driving motor 166 measured by the rotary encoder 165 is transmitted into the control unit 600. The control unit 600 may calculate a position of the buffer dancer roller 150 and a length of the moving path of the object T according to the position of the buffer dancer roller 150 from the measured values of the rotary encoder 165.

Although the rotary encoder 165 is described as constituting the buffer dancer roller position detection part in the current embodiment, any device which is capable of detecting the position of the buffer dancer roller 150 may be used as the buffer dancer roller position detection part. For example, a linear encoder which is capable of directly detecting the position of the buffer dancer roller 150 may be used as the buffer dancer roller position detection part.

The buffer dancer roller 150 and the weight balancing part 160 may be disposed between the unwinding unit 100 and the first inspection unit 200, between the first inspection unit 200 and the second inspection unit 300, between the second inspection unit 300 and the marking unit 400, and between the marking unit 400 and the winding unit 500, according to exemplary embodiments. As described above, the buffer dancer roller 150 and other buffer dancer rollers 250, 350, and 450, as described below, may be disposed between the working units 100, 200, 300, 400, and 500 to maintain the tension of the object T over the reel-to-reel inspection apparatus 1. Also, the control unit 600 may control the position of the buffer dancer roller 150 to adjust a length of the object T between the respective working units 100, 200, 300, 400, and 500. Thus, the working units 100, 200, 300, 400, and 500 may be synchronized in operation. For example, when about 20.5 inspection areas exist on the object T disposed between the first inspection unit 200 and the second inspection unit 300, the object T may increase or decrease in length by moving the buffer dancer roller 150. As a result, the integer number of inspection areas, for example, about 20 inspection areas or about 21 inspection areas exist on the object T disposed between the first inspection unit 200 and the second inspection unit 300. Thus, inspection on the inspection areas of the object T in the first and second inspection units 200 and 300 may be performed simultaneously. As described above, the control unit 600 may synchronize operations of the preceding and following working units by using the information with respect to the object T and the position information of the buffer dancer roller 150.

The first inspection unit 200 accommodates the object T unwound from the unwinding unit 100 to inspect a surface of the object T, e.g., a top surface of the object T.

Figure 5:
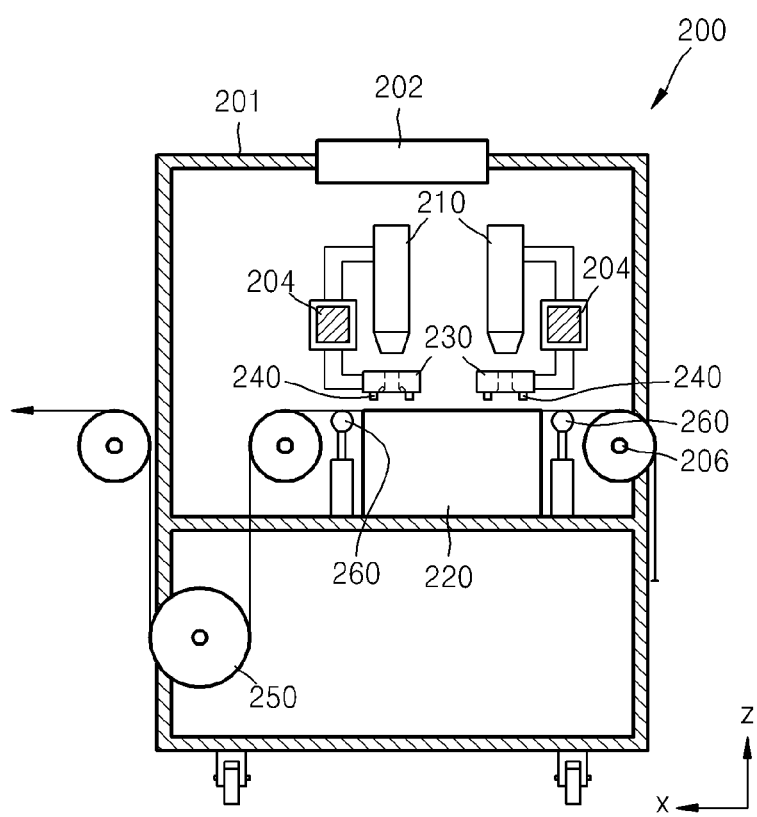
FIG. 5 is a schematic view illustrating a first inspection unit of the reel-to-reel inspection apparatus of FIG. 1, according to an exemplary embodiment.

FIG. 5 is a schematic view illustrating an inner structure of the first inspection unit 200. Referring to FIG. 5, the first inspection unit 200 includes a housing 201, a first camera 210, a first vacuum plate 220, a lighting part 230, an air blower 240, and a first reciprocating roller 260.

The housing 201 has an inner space which is capable of accommodating the first camera 210, the first vacuum plate 220, the lighting part 230, the air blower 240, and the first reciprocating roller 260. A HEPA filter 202 may be disposed in an upper portion of the housing 202. The HEPA filter 202 performs substantially the same function as the HEPA filter 102 of the unwinding unit 100.

The first camera 210 is disposed above the object T. Also, the first camera 210 is coupled to an LM guide 204 extending in a width direction of the object T to scan and photograph inspection areas of the object T while being moved along the LM guide 204. A plurality of the first cameras 210 may be provided to obtain images of a plurality of inspection areas at the same time. The first camera 210 may be a line scan camera.

The first vacuum plate 220 is a portion on which the object T is disposed and seated. The first vacuum plate 220 has a plurality of absorption holes 222 (shown in FIG. 6) at a top surface thereof to absorb the object T seated on the top surface of the first vacuum plate 220. When air is sucked through the absorption holes 222 in a state where the object T is seated on the top surface of the first vacuum plate 220, the object T sticks to the first vacuum plate 220. Thus, the object T may be stably fixed and flatly spread.

The lighting part 230 emits light onto the object T so that the first camera 210 obtains images of the object T. The lighting part 230 may be coupled to the LM guide 204 and integrally moved together with the first camera 210.

Figure 6:
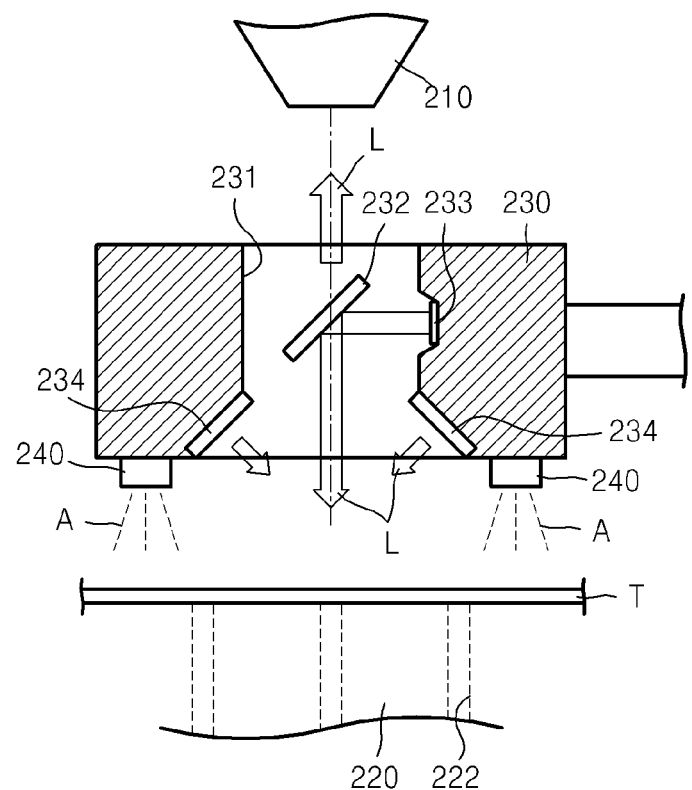
FIG. 6 is a schematic view illustrating a lighting part of the reel-to-reel inspection apparatus of FIG. 1, according to an exemplary embodiment.

FIG. 6 is a schematic view illustrating an inner structure of the lighting part 230. Referring to FIG. 6, the lighting part 230 is disposed between the first camera 210 and the object T. Also, the lighting part 230 has an opening 231 along a path of incident light of the first camera 210. The lighting part 230 includes a translucent mirror 232, a side lighting unit 233, and a downward lighting unit 234.

The translucent mirror 232 is disposed within an opening 231 of the lighting part 230. Also, the translucent mirror 232 may be obliquely disposed at an angle of about 45 degrees on the path of the incident light of the first camera 210. The translucent mirror 232 reflects light incident from a lateral side toward a lower side and allows light incident from the lower side to pass through an upper side.

The side lighting unit 233 laterally emits light L toward the translucent mirror 232. Thus, the light L of the side lighting unit 233 is reflected by the translucent mirror 232 and thus emitted onto the object T. As described above, since the light L of the side lighting unit 233 is emitted onto the object T along an optical axis line of the first camera 210 via the translucent mirror 232, the light L may very uniformly emitted onto the inspection areas of the object T to be photographed by the first camera 210.

The downward lighting unit 234 is disposed under the lighting part 230 to emit light L toward the object T. The downward lighting unit 234 obliquely emits the light L onto the inspection areas of the object T.

The air blower 240 may spray air A toward the object T to remove foreign matters existing on the top surface of the object T. The air blower 240 may be coupled to the lighting part 230 to spray the air A toward the object T while being moved together with the lighting part 230. That is, the air blower 240 may be moved together with the lighting part 230 and the first camera 210. The air blower 240 may spray the air A onto the object T before the first camera photographs the object T to remove the foreign matters existing on the inspection areas of the object T.

The first reciprocating roller 260 is disposed on each of front and rear sides of the first vacuum plate 220. The first reciprocating roller 260 is movably disposed between a first position at which the object T is seated on a first vacuum plate 220 and a second position at which the object T is separated from the first vacuum plate 220.

Figure 7:
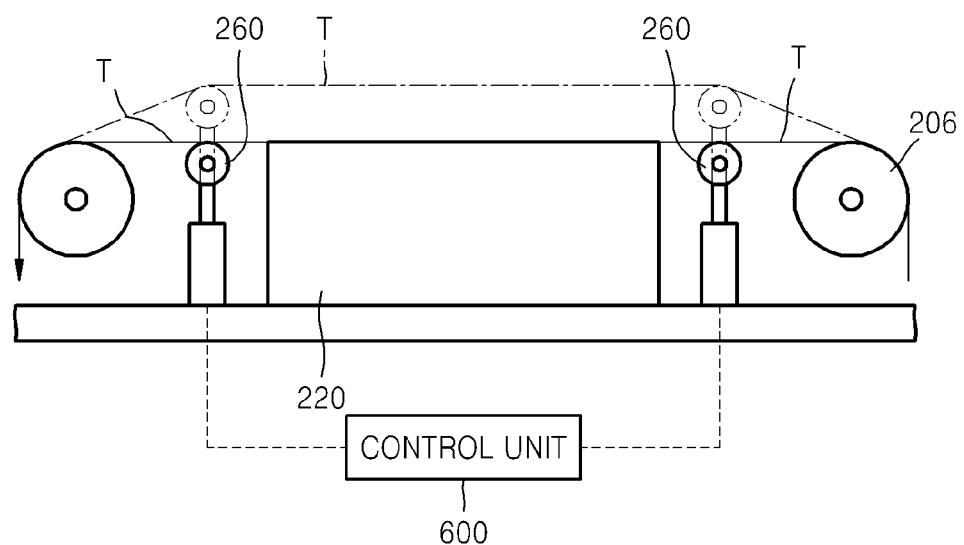
FIG. 7 is a schematic view illustrating a process in which an object is seated on a vacuum plate in the first inspection unit of the reel-to-reel inspection apparatus of FIG. 1, according to an exemplary embodiment.

FIG. 7 is a schematic view illustrating a process in which the first reciprocating roller 260 seats and separates the object T on/from the first vacuum plate 220. As shown as a solid line in FIG. 7, when the first reciprocating roller 260 is disposed at the same height as a top surface of the first vacuum plate 220 or at a height less than that of the top surface of the first vacuum plate 220, the object T contacts the top surface of the first vacuum plate 220. In this state, the first vacuum plate 220 absorbs the object T to fix or planarize the object T. When the object T is fixed to the first vacuum plate 220, the air blower 240 removes the foreign matters from the top surface of the object T, and the lighting part 230 and the first camera 210 scans the inspection areas of the object T, thereby obtaining inspection images. When the inspection areas of the object T are completely photographed, the absorption force of the first vacuum plate 220 may be removed. As shown as an alternate long and short dash line in FIG. 7, the first reciprocating roller 260 ascends to separate the object T from the first vacuum plate 220. When the object T is separated from the first vacuum plate 220, the object T may be transferred again, and then the same process as the above-described processes may be repeatedly performed for other inspection areas. The above-described processes may be automatically controlled by the control unit 600.

Figure 8:
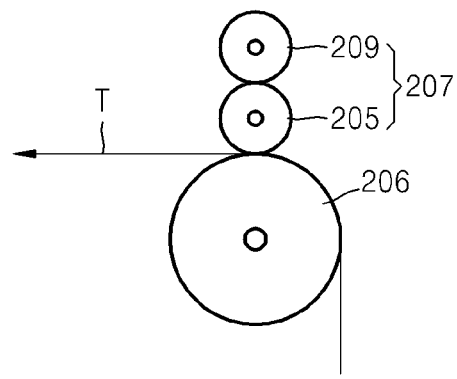
FIG. 8 is a schematic view illustrating a part removing foreign matters before an object is photographed within the first inspection unit in the reel-to-reel inspection apparatus of FIG. 1, according to an exemplary embodiment.

The object T may pass through a foreign matter removing roller before the object T is introduced onto the first vacuum plate 220. FIG. 8 is a schematic view of a foreign matter removing roller 207. The foreign matter removing roller 207 is disposed on a front side of the first vacuum plate 220 on a transfer path of the object T. The foreign matter removing roller 207 may be disposed such that the object T is disposed between the foreign matter removing roller 207 and the transfer roller 206 contacting a bottom surface of the object T. The foreign matter removing roller 207 may include a contact roller 205 and an adhesion roller 209. The contact roller 205 directly contacts the top surface of the object T. The contact roller 205 may be formed of a resin material, for example, a silicone resin material. The contact roller 205 may directly contact the object T to remove foreign matters existing on the object T. The adhesion roller 209 contacts the contact roller 205. Also, the adhesion roller 209 is coated with a material having an adhesion on a surface thereof such as an adhesion tape. Since the adhesion roller 209 has an adhesion greater than that of the contact roller 205, the foreign matters attached to the contact roller 205 may be separated by the adhesion roller 209. Thus, the contact roller 205 may be maintained in a clean state.

As described above, since the foreign matters are previously removed by using the foreign matter removing roller 207 before the object T is placed onto the first vacuum plate 220, misjudgment of a product state which may occur when foreign matters remaining on the object T are displayed on an image photographed by the first camera 210 may be effectively reduced.

The object T photographed by the first camera 210 is introduced into the second inspection unit 300 via the buffer dancer roller 250. The buffer dancer roller 250 disposed between the first inspection unit 200 and the second inspection unit 300 may also be adequately adjusted with regard to pressure and position by a weight balancing part similar to weight balancing part 160 illustrated in FIG. 4.

Figure 9:
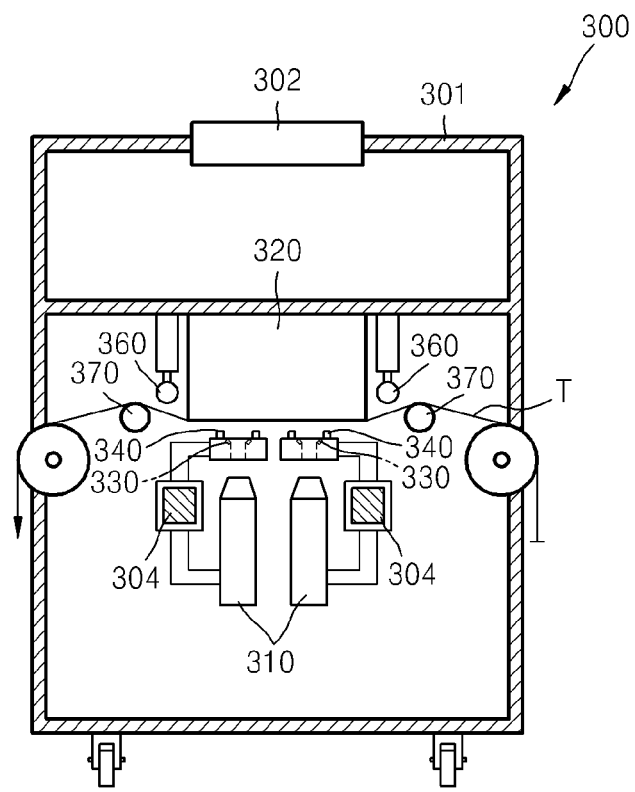
FIG. 9 is a schematic view illustrating a second inspection unit of the reel-to-reel inspection apparatus of FIG. 1, according to an exemplary embodiment.

The second inspection unit 300 inspects a surface opposite to the surface of the object T inspected by the first inspection unit 200, i.e., the bottom surface of the object T. FIG. 9 is a schematic view illustrating an inner structure of the second inspection unit 300. Referring to FIG. 9, the second inspection unit 300 includes a housing 301, a second camera 310, a second vacuum plate 320, a lighting part 330, an air blower 340, a second reciprocating roller 360, and an auxiliary press roller 370.

The housing 301 has an inner space which is capable of accommodating the second camera 310, the second vacuum plate 320, the lighting part 330, the air blower 340, the second reciprocating roller 360, and the auxiliary press roller 370. A HEPA filter 302 may also be disposed in an upper portion of the housing 301. The HEPA filter 302 performs substantially the same function as the HEPA filter 102 of the unwinding unit 100.

The second camera 310 of the second inspection unit 300, the second vacuum plate 320, the lighting part 330, the air blower 340, the second reciprocating roller 360 may correspond to the first camera 210 of the first inspection unit 200, the first vacuum plate 220, the lighting part 230, the air blower 240, and the first reciprocating roller 260, respectively. Also, the second camera 310 of the second inspection unit 300, the second vacuum plate 320, the lighting part 330, the air blower 340, the second reciprocating roller 360 are respectively disposed symmetrical to the first camera 210 of the first inspection unit 200, the first vacuum plate 220, the lighting part 230, the air blower 240, and the first reciprocating roller 260 so that the bottom of the object T is inspected. The second camera 310 of the second inspection unit 300, the second vacuum plate 320, the lighting part 330, the air blower 340, the second reciprocating roller 360 may be disposed on sides opposite to those of the first camera 210 of the first inspection unit 200, the first vacuum plate 220, the lighting part 230, the air blower 240, and the first reciprocating roller 260, respectively. Thus, their duplicated descriptions will be omitted.

The auxiliary press roller 370 is disposed at each of front and rear sides of the second vacuum plate 320 on a travelling path of the object T. Also, the auxiliary press roller 370 is disposed above a surface of the second plate 320 to which the object T is absorbed. Thus, the auxiliary press roller 370 may upwardly push both sides of the object T corresponding to both sides of the second vacuum plate 320 so that both sides of the object T are disposed above the surface of the second vacuum plate 320. The auxiliary press roller 370 may be fixed in position. Alternatively, the auxiliary press roller 370 may ascend or descend. Here, when the auxiliary press roller 370 ascends, the auxiliary press roller 370 may be disposed above the surface of the second vacuum plate 320 to push both sides of the object T upward. As described above, since the auxiliary press roller 370 pushes both sides of the object T upward with respect to a center of the second vacuum plate 320, the object T may be more effectively attached to the second vacuum plate 320. Also, when the second vacuum plate 320 absorbs the object T in the state where the auxiliary press roller 370 pushes the object T toward the second vacuum plate 320, the object T may be further closely attached to the second vacuum plate 320.

If the auxiliary press roller 370 is not provided, the object T droops down by its self-weight. Thus, when the object T is absorbed onto the second vacuum plate 320 in the state where the object T droops down, the object T may wrinkle. When the object T wrinkles, the object T may be damaged, or the vision inspection is not performed properly. Thus, it is necessary to prevent the object T from wrinkling. To prevent the object T from drooping down, the pressures of the buffer dancer rollers 150, 250, 350, and 450 may increase to increase the tensile force applied to the object T. However, if the tensile force applied to the object T increases, the object T may be damaged. In addition, the drooping of the object T may not be effectively reduced.

On the other hand, in the current embodiment, the second inspection unit 300 may include the auxiliary press roller 370 to push both sides of the object T upward, thereby effectively reducing the drooping of the object T. Thus, the object T may be more closely attached to the second vacuum plate 320 to effectively prevent the object T from wrinkling during the absorption of the object T onto the second vacuum plate 320.

When the object T is adhered onto the second vacuum plate 320, the second camera 310 scans the inspection areas of the object T while moving along the LM guide 304 to obtain images with respect to the inspection areas of the object T. Then, the images photographed by the second camera 310 are transmitted to the control unit 600. The control unit 600 determines whether defects exist on the inspection areas on the basis of the images.

Also, a part similar to the foreign matter removing roller 207 of the first inspection unit 200 may be provided on a front side of the second vacuum plate 320 of the second inspection unit 300 to remove foreign matters existing on the bottom surface of the object T.

When the scanning of the second camera 310 is completed, the absorption force of the second vacuum plate 320 is removed. Then, the second reciprocating roller 360 is moved downward to separate the object T from the second vacuum plate 320. When the object T is separated from the second vacuum plate 320, the object T may be transferred again.

The object T may gradually advance along the transfer path and be introduced into the marking unit 400 via the buffer dancer roller 350. Here, the buffer dancer roller 350 may have the same configuration as the above-described buffer dancer roller 150.

Figure 10:
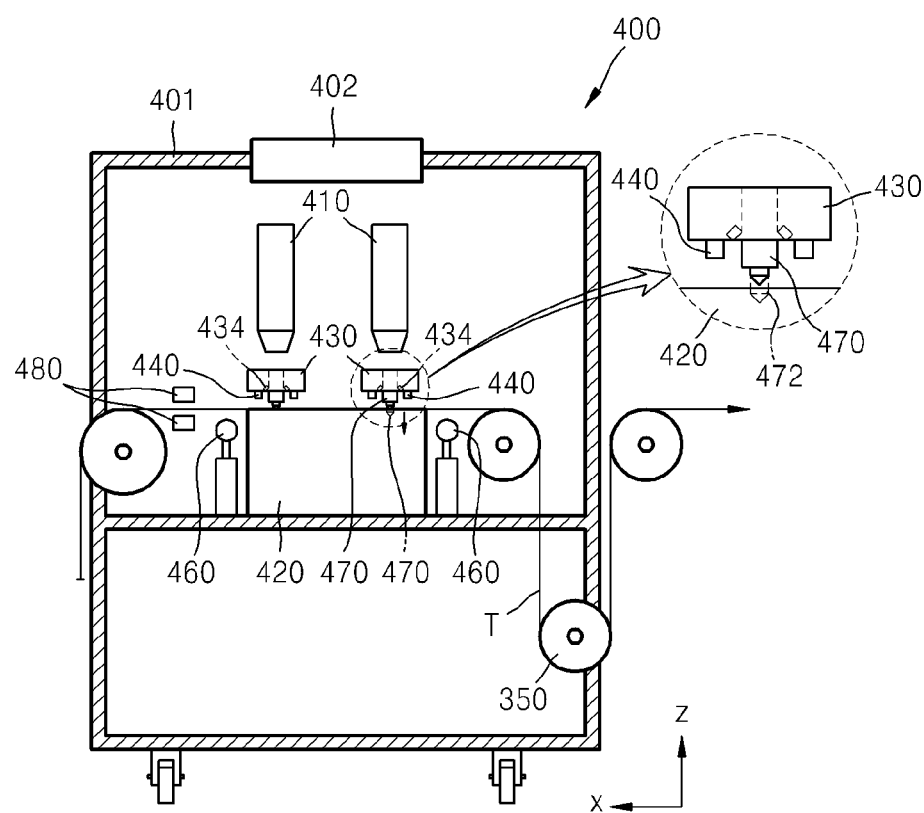
FIG. 10 is a schematic view illustrating a marking unit of the reel-to-reel inspection apparatus of FIG. 1, according to an exemplary embodiment.

The marking unit 400 may display whether defects exist on the inspection areas of the object T on the object T. FIG. 10 is a schematic view illustrating an inner structure of the marking unit 400. Referring to FIG. 10, the marking unit 400 includes a housing 401, a third camera 410, a third vacuum plate 420, a lighting part 430, a marker 470, an air blower 440, a reciprocating roller 460, and a magnetic substance removing part 480.

The housing 401 has an inner space which is capable of accommodating the third camera 410, the third vacuum plate 420, the lighting part 430, the air blower 440, the marker 470, the reciprocating roller 460, and the magnetic substance removing part 480. Like the above-described working units, a HEPA filter 402 may also be disposed in an upper portion of the housing 401.

The third camera 410 photographs the inspection areas of the object T. Also, the third camera 410 may confirm the alignment of the object T. It does not matter whether a resolution of the third camera 410 is high, unlike the first and second cameras 210 and 310. For example, the third camera may not be a line scan camera, but a common camera for photographing a flatbed image.

The lighting part 430 includes a light emitting part 434. The light emitting part 434 emits light onto the object T so that the third camera 410 photographs the object T. The lighting part 430 may be disposed between the third camera 410 and the object T. Also, the lighting part 430 may have an opening for securing a clear view of the third camera 410.

The air blower 440 sprays air onto the object T to remove foreign matters existing on the surface of the object T. The air blower 440 may be disposed under the lighting part 430.

The marker 470 marks whether defects exist on the object T. The marker 470 is disposed at a position corresponding to a marking area of the object T, for example, at a position corresponding to an edge in a width direction of the object T. Also, the marker 470 is disposed outside a path of light incident into the third camera 410 to prevent the third camera from being blocked. When it is determined that defects exist on the inspection areas of the object T, the marker 470 marks a distinguishable mark on the marking area. The marker 470 may perform the marking by using various methods such as mechanical punching, laser marking, distinguishable material coating, and the like. In the current embodiment, the mechanical punching will be described as one example. That is, when the inspection areas of the object T on which it is determined that the defects exist reaches the marker 470, a tip 472 of the maker 470 descends to push the object T, thereby marking the distinguishable mark.

When the marking process with respect to the object T is completed by the marker 470, the reciprocating roller 460 ascends to separate the object T from the third vacuum plate 420. When the object T is separated from the third vacuum plate 420 by the reciprocating roller 460, the object T may be transferred again. The transferred object T is introduced into the winding unit 500 via the buffer dancer roller 450. Here, the buffer dancer roller 450 may have the same configuration as the above-described buffer dancer roller 150.

Figure 11:
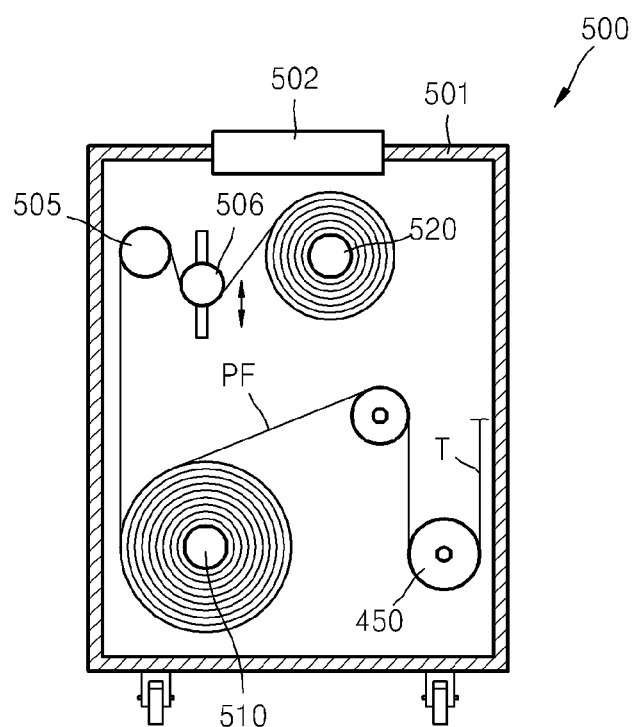
FIG. 11 is a schematic view illustrating a winding unit of the reel-to-reel inspection apparatus of FIG. 1, according to an exemplary embodiment.

The winding unit 500 winds the object on which the vision inspection and the marking are performed in a roll shape. FIG. 11 is a schematic view illustrating an inner structure of the winding unit 500. Referring to FIG. 11, the winding unit 500 includes a housing 501, a roll mount part 510, and a protection film mount part 520.

The housing provides an inner space which is capable of accommodating the roll mount part 510 and the protection film roll mount part 520. Like the above-described working units, a HEPA filter 502 may also be disposed in an upper portion of the housing 501.

The roll mount part 510 winds the object T in the roll shape. The roll mount part 510 of the winding unit 500 is different from the roll mount part 110 of the unwinding unit 100 only in that the roll mount part 510 winds the object T. However, the roll mount part 510 of the winding unit 500 has the same structure as the roll mount part 110 of the unwinding unit 100. Thus, their duplicated descriptions will be omitted.

The protection film roll mount part 520 unwinds the protection film PF so that the protection film PF is covered again on a surface of the object T before the object T is wound around the winding unit 500. The protection film roll mount part 520 is different from the protection film roll mount part 120 of the unwinding unit 100 only in that the protection film roll mount part 520 unwinds the protection film PF. The protection film roll mount part 520 has the same structure as the protection film roll mount part 120.

The protection film PF wound around the protection film roll mount part 120 may be attached to the surface of the object T via the buffer dancer rollers 505 and 506. The buffer dancer rollers 505 and 506 adjust a tensile force of the protection film PF and change a moving path of the protection film PF. At least one roller 506 of the buffer dancer roller 505 and 506 may be movably disposed.

Through the above-described processes, the protection film PF is attached to the surface of the object T, and the object T is wound again in the roll shape. Thus, when the inspection processes with respect to the object T are completed, the object T may be distributed in the roll shape.

The control unit 600 automatically controls the unwinding unit 100, the first inspection unit 200, the second inspection unit 300, the marking unit 400, and the winding unit 500. The control unit 600 may be a computer including a micro processer. Also, the control unit 600 may control a moving speed of the object T and synchronize the operations of the working units 100, 200, 300, and 400.

Figure 12:
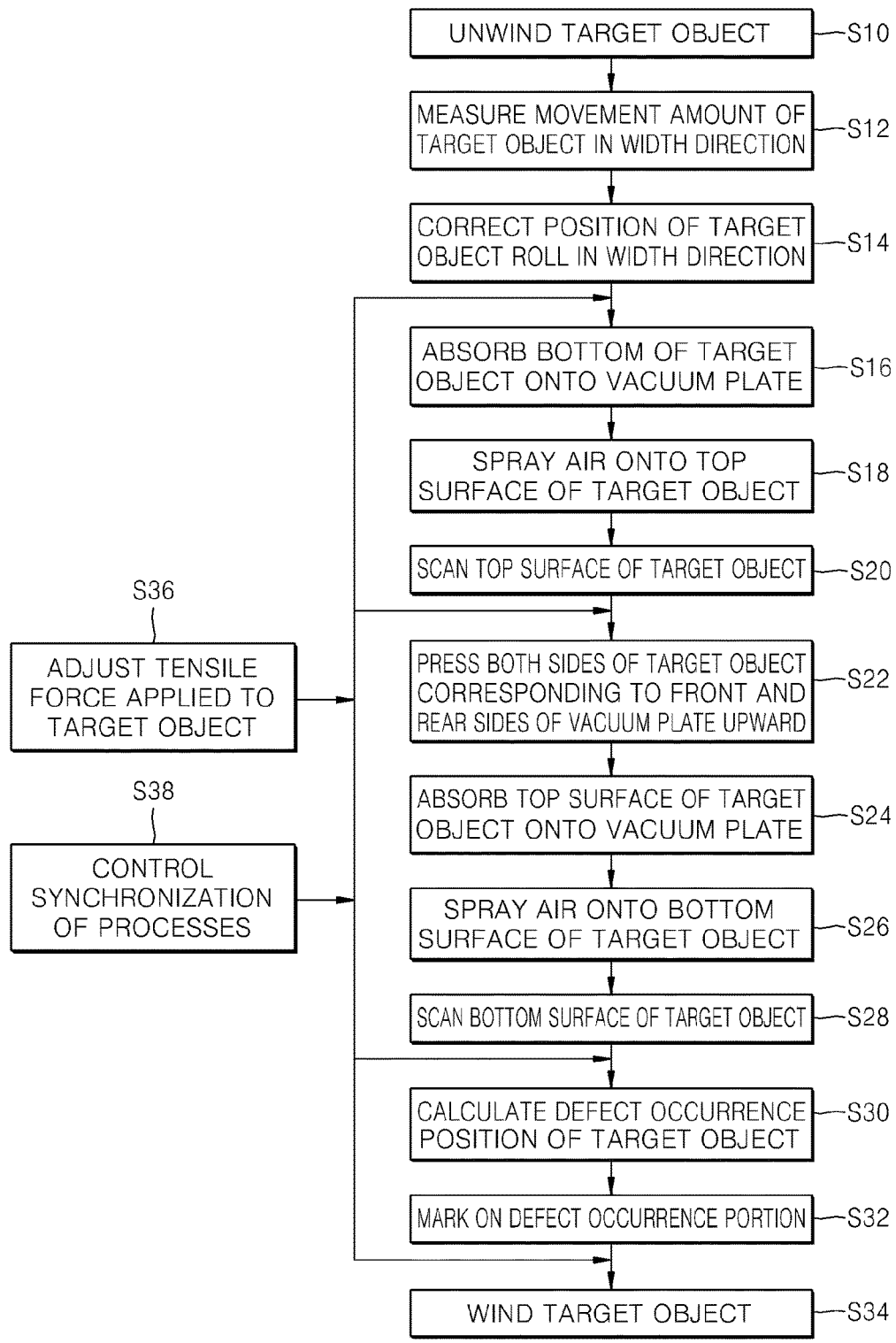
FIG. 12 is a schematic flowchart of a reel-to-reel inspection method according to an exemplary embodiment.

As described above, a reel-to-reel inspection method using the reel-to-reel inspection apparatus may, as shown in FIG. 12, include: unwinding an object T in an unwinding unit (S10); measuring a movement amount in a width direction of the object T in an alignment inspection part 130 (S12); correcting a position of the roll mount part 110 to correct a position in a width direction of a roll of the object T (S14); adhering a bottom surface of the object T onto a first vacuum plate 220 in a first inspection unit 200 (S16); spraying air onto a top surface of the object T adhered to the first vacuum plate 220 of the first inspection unit 200 to remove foreign matters (S18); emitting light onto the top surface of the object T adhered to the first vacuum plate 220 of the first inspection unit 200 to scan the top surface of the object T (S20); locating a second vacuum plate 320 above the object T in the second inspection unit 300 to press both sides of the object T corresponding to front and rear sides of the second vacuum plate 320 upward (S22); adhering the top surface of the object T onto the second vacuum plate 320 in the second inspection unit 300 (S24); spraying air onto the bottom surface of the object T absorbed on the second vacuum plate 320 to remove foreign matters in the second inspection unit 300 (S26); emitting light onto the bottom surface of the object T adhered to the second vacuum plate 320 of the second inspection unit 300 to scan the bottom surface of the object T (S28); determining whether defects exist on the object T by using image information of the top and bottom surfaces of the object T obtained from the first and second inspection units 200 and 300 in the control unit to calculate positions of the defects (S30); performing a marking process on the object T on which the defects exist in the marking unit 400 (S32); and winding the object on which the marking process is performed in the winding unit 500 (S34).

Also, while the above-described processes are performed, a process of adjusting a tensile force applied to the object T may be performed by using buffer dancer rollers 150, 250, 350, and 450.

The respective processes may be performed in the unwinding unit 100, the first inspection unit 200, the second inspection unit 300, the marking unit 400, and the winding unit 500 at the same time. That is, the scanning (S20) of the top surface of the object T in the first inspection unit 200, the scanning (S28) of the bottom surface of the object T in the second inspection unit 300, and the marking of the object T in the marking unit 400 may be performed on inspection areas of other objects T at the same time. To perform the above-described processes in each of the working units at the same time, the reel-to-reel inspection method according the current embodiment may further include synchronizing the processes (S38). To synchronize the processes, the buffer dancer rollers 150, 250, 350, and 450 may be adjusted in a position to adjust a length of the object T between the working units 100, 200, 300, 400, and 500 as described above.

Although the starting, proceeding, and finishing of each of the processes may be performed by a direct control of a user, the starting, proceeding, and finishing of each of the processes may be automatically performed by a control unit 600.

When the roll-shaped object T is inspected by using the reel-to-reel inspection apparatus 1 according to the embodiments, the top and bottom surfaces of the object T may be inspected at the same time without turning over the object T. Thus, the inspection process may be simply and quickly performed. Also, the object T may be inspected in the first and second inspection units 200 and 300 at the same time by using a plurality of cameras. Furthermore, since the foreign matters on the object T may be removed while the inspection process is performed, the inspection process speed of the object T may be further improved. Particularly, the reel-to-reel inspection apparatus 1 according to the embodiments may perform the inspection process at a high speed even though the object T has a wide width.

Although the reel-to-reel inspection apparatus 1 and the reel-to-reel inspection method using the same are described as described above, the inventive concept is not limited thereto. That is, the inventive concept may be embodied in various structures and methods.

For example, although the top surface of the object T is scanned first and the bottom surface of the object T is scanned later in the foregoing embodiment, the inventive concept is not limited thereto. For example, the bottom surface may be scanned first, and then, the top surface may be scanned later. In this case, the first and second inspection units 200 and 300 may be exchanged in position.

Also, the first and second cameras 210 and 310 may be movably disposed in the transfer direction of the object T as well as in the width direction of the object T. In this case, the first and second cameras 210 and 310 may scan the object T in a zigzag shape to photograph more wide areas of the object T at once.

Also, although the buffer dancer rollers 150, 250, 350, and 450 press the object T by using the pulley 164, the belt 163, and the weight 161, the buffer dancer rollers 150, 250, 350, and 450 may press the object T by using a static load spring.

Also, although the two first reciprocating rollers 260 are disposed on both sides of the first vacuum plate 220, the first reciprocating roller 260 may be disposed on only one side of the first vacuum plate 220, and a fixed roller may be disposed on the other side of the first vacuum plate 220. In this case, the object T may be spaced from the first vacuum plate 220 by the first reciprocating roller 260. Similarly, it may be unnecessary to provide the two second reciprocating rollers 360.

In addition, the inventive concept may be embodied in various structures and methods.

According to the reel-to-reel inspection apparatus and the reel-to-reel inspection method, both surfaces of the roll-shaped object may be inspected at the same time. Also, the inspection process of the object may be simply and quickly performed, thereby improving the process productivity.

While the inventive concept has been particularly shown and described with reference to exemplary embodiments thereof, it will be understood by those of ordinary skill in the art that various changes in form and details may be made therein without departing from the spirit and scope of the inventive concept as defined by the following claims.

What is claimed is:

1. A reel-to-reel inspection apparatus comprising:
an unwinder configured to unwind a roll-shaped object;
a first inspector configured to photograph a first surface of the object discharged from the unwinder;

a second inspector configured to photograph a second surface opposite to the first surface of the object which has passed through the first inspector;
a buffer dancer roller configured to press the object disposed at least one portion between the unwinder, the first inspector, the second inspector, and the winder to apply a tensile force to the object;
a marker configured to indicate a mark on the object which has passed through the second inspector unit;
a winder configured to wind in a roll shape the object which has passed through the marker; and
a controller configured to synchronize at least two operations of unwinding roll-shaped object by the unwinder, photographing the first surface of the object by the first inspector, photographing the second surface of the object by the second inspector, indicating the mark by the marker, and winding in the roll shape the object by the winder, based on position information about the buffer dancer roller in a directing crossing a moving path of the object.

2. The reel-to-reel inspection apparatus of claim 1, wherein the weight balancing part comprises:
a belt connected to a side of the buffer dancer roller;
a pulley configured to drive the belt so that the buffer dancer roller connected to a first side of the belt is moved; and
a weight connected to a second side opposite to the first side of the belt to apply a force into the buffer dancer roller in a direction opposite to gravity.

3. The reel-to-reel inspection apparatus of claim 1 further comprising a weight balancing part,
wherein the buffer dancer roller is configured to press the object through its weight, and
wherein the weight balancing part is configured to apply a force to the buffer dancer roller in a direction opposite to gravity to offset the portion of the weight of the buffer dancer roller.

4. The reel-to-reel inspection apparatus of claim 1, wherein the buffer dancer roller is disposed to be movable in a direction crossing a transfer direction of the object, and
wherein the reel-to-reel inspection apparatus further comprises a detection part configured to detect a position of the buffer dancer roller.

5. The reel-to-reel inspection apparatus of claim 4, further comprising:
a belt having a side connected to the buffer dancer roller; and
a pulley configured to drive the belt to move the buffer dancer roller connected to the belt,
wherein the detection part comprises a rotary encoder disposed on the pulley.

6. A reel-to-reel inspection apparatus comprising:
an unwinder configured to unwind a roll-shaped object;
a first inspector configured to photograph a first surface of the object discharged from the unwinder;
a second inspector configured to photograph a second surface opposite to the first surface of the object which has passed through the first inspector;
a marker configured to indicate a mark on the object which has passed through the second inspector; and
a winder configured to wind in a roll shape the object which has passed through the marker,
wherein the unwinder comprises:
a roll mount part configured to mount the object and move in a width direction of the object;
an alignment inspection part configured to detect a movement of the object in a direction crossing an unwinding direction the object; and
a control part configured to move the roll mount part in response to the movement of the object detected by the alignment inspection part.

7. The reel-to-reel inspection apparatus of claim 6, wherein the roll mount part of the unwinder is configured to vacuum-absorb the object.

8. A reel-to-reel inspection apparatus comprising:
an unwinder configured to unwind a roll-shaped object;
a first inspector configured to photograph a first surface of the object discharged from the unwinder;
a second inspector configured to photograph a second surface opposite to the first surface of the object which has passed through the first inspector;
a marker configured to indicate a mark on the object which has passed through the second inspector; and
a winder configured to wind in a roll shape the object which has passed through the marker,
wherein the first inspector comprises:
a first camera configured to photograph the first surface of the object; and
a first vacuum plate configured to absorb the second surface of the object,
wherein the second inspector comprises:
a second camera configured to photograph the second surface of the object; and
a second vacuum plate configured to absorb the first surface of the object.

9. The reel-to-reel inspection apparatus of claim 8, wherein the second vacuum plate of the second inspector is disposed above the object,
wherein the second camera of the second inspector is disposed under the object, and
wherein the reel-to-reel inspection apparatus further comprises an auxiliary press roller upwardly pushing at least one side of the object corresponding to at least one side of the second vacuum plate so that the at least one side of the object is disposed at a position higher than that of a surface of the second vacuum plate.

10. The reel-to-reel inspection apparatus of claim 8, wherein the first inspector comprises a first reciprocating roller disposed on at least one side of front and rear sides of the first vacuum plate and disposed to be movable between a first position at which the object contacts the first vacuum plate and a second position at which the object is spaced from the first vacuum plate, and
wherein the second inspector comprises a second reciprocating roller disposed on at least one side of front and rear sides of the second vacuum plate and disposed to be movable between a first position at which the object contacts the second vacuum plate and a second position at which the object is spaced from the second vacuum plate.

11. The reel-to-reel inspection apparatus of claim 8, wherein at least one of the first and second cameras is disposed to be movable in at least one direction of a length direction of the object and a width direction of the object,
wherein the reel-to-reel inspection apparatus further comprises a lighting part coupled to at least one of the first and second cameras and integrally moving with the at least one camera to emit light onto the object.

12. The reel-to-reel inspection apparatus of claim 11, wherein the lighting part comprises:
a translucent mirror disposed between at least one of the first and second cameras and the object; and a side light configured to emit light onto the translucent mirror, wherein the light emitted from the side light is reflected by the translucent mirror onto the object, and wherein the light reflected by the object passes through the translucent mirror and is incident onto at least one of the first and second cameras.

13. The reel-to-reel inspection apparatus of claim 11, further comprising an air blower coupled to at least one of the first and second cameras and integrally moving with the at least one camera to spray air onto the object.

14. A reel-to-reel inspection method comprising:

unwinding a roll-shaped object;

photographing a first surface of the unwound object to inspect the first surface;

photographing a second surface opposite to the first surface of the object to inspect the second surface;

providing a buffer dancer roller movably to be disposed in a direction crossing a moving path of the object to increase or decrease a length of the moving path of the object;

detecting a position of the buffer dancer roller in the direction crossing the moving path of the object; and determining whether a defect exists on the object according to inspection results of the inspecting the first and the second surfaces;

marking existence or nonexistence of the defect on the object after the determining;

winding the object, on which the existence or nonexistence of the defect is marked, in a roll shape; and synchronizing at least two operations of the unwinding the roll-shaped object, the photographing the first surface of the object, the photographing the second surface of the object, the determining whether the defect exists, the marking the existence or nonexistence, and winding the object, based on information about the detected position of the buffer dancer roller.

15. The reel-to-reel inspection method of claim 14, wherein at least one of the inspecting the first surface and the inspecting the second surface comprises scanning the object while an inspection apparatus for the inspecting is moving in length and width directions of the object, and wherein the scanning the object comprises removing foreign matters from at least one of the first surface and the second surface of the object by using a blower coupled to the inspection apparatus and integrally moving with the camera.

16. The reel-to-reel inspection method of claim 14, further comprising:

absorbing the object onto a first vacuum plate to inspect the first surface; and absorbing the object onto a second vacuum plate to inspect the second surface.

* * * * *